United States Patent [19]

Lescrenier

[11] 4,293,771
[45] Oct. 6, 1981

[54] INDICATOR FOR USE WITH PROJECTED BEAM OF RADIATION

[76] Inventor: Charles Lescrenier, 660 Crescent Ct., Wauwatosa, Wis. 53213

[21] Appl. No.: 46,435

[22] Filed: Jun. 7, 1979

[51] Int. Cl.³ .................. G01N 21/00; G01N 23/00
[52] U.S. Cl. .................................. 250/491; 356/138
[58] Field of Search ............... 250/490, 491, 492 R, 250/445 T; 356/153, 138

[56] References Cited

U.S. PATENT DOCUMENTS

| 4,117,337 | 9/1978 | Staats | 250/491 |
| 4,132,900 | 1/1979 | Smith | 250/491 |

Primary Examiner—David K. Moore
Assistant Examiner—T. N. Grigsby
Attorney, Agent, or Firm—Andrus, Sceales, Starke & Sawall

[57] ABSTRACT

An indicator for defining the relationship of a radiation beam to an object, such as a patient or associated apparatus, for example an X-ray film holder. The indicator includes a light source establishing a first light plane containing the beam and appliable to the object. A second light source establishes a second plane of light to contain the radiation beam or object. The intersection of the beams of light defines the radiation beam-object relationship.

13 Claims, 4 Drawing Figures

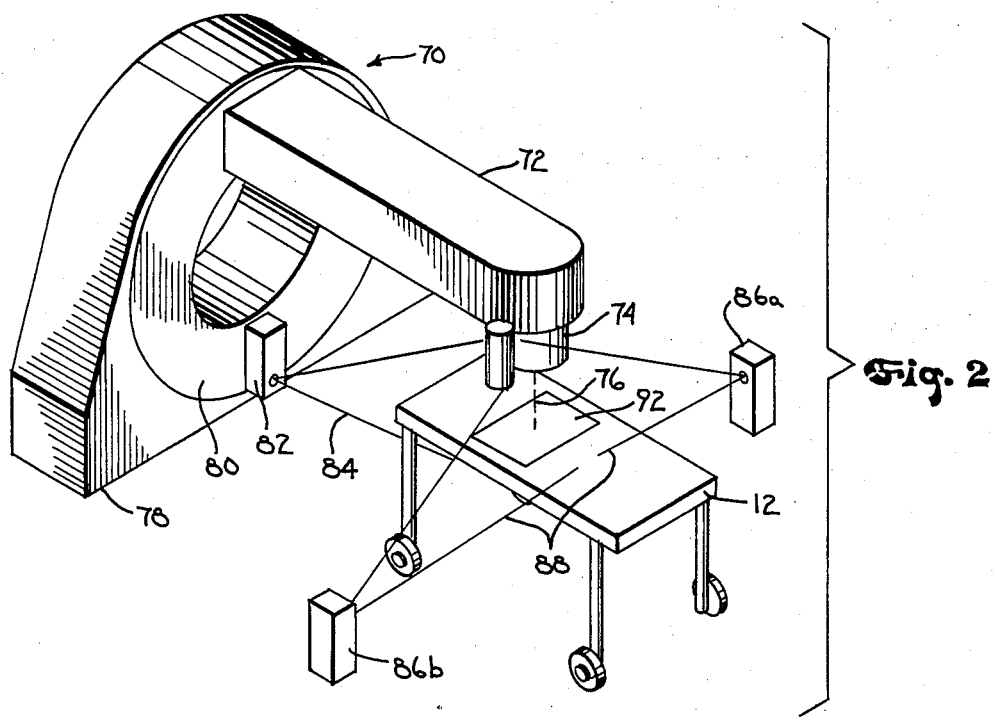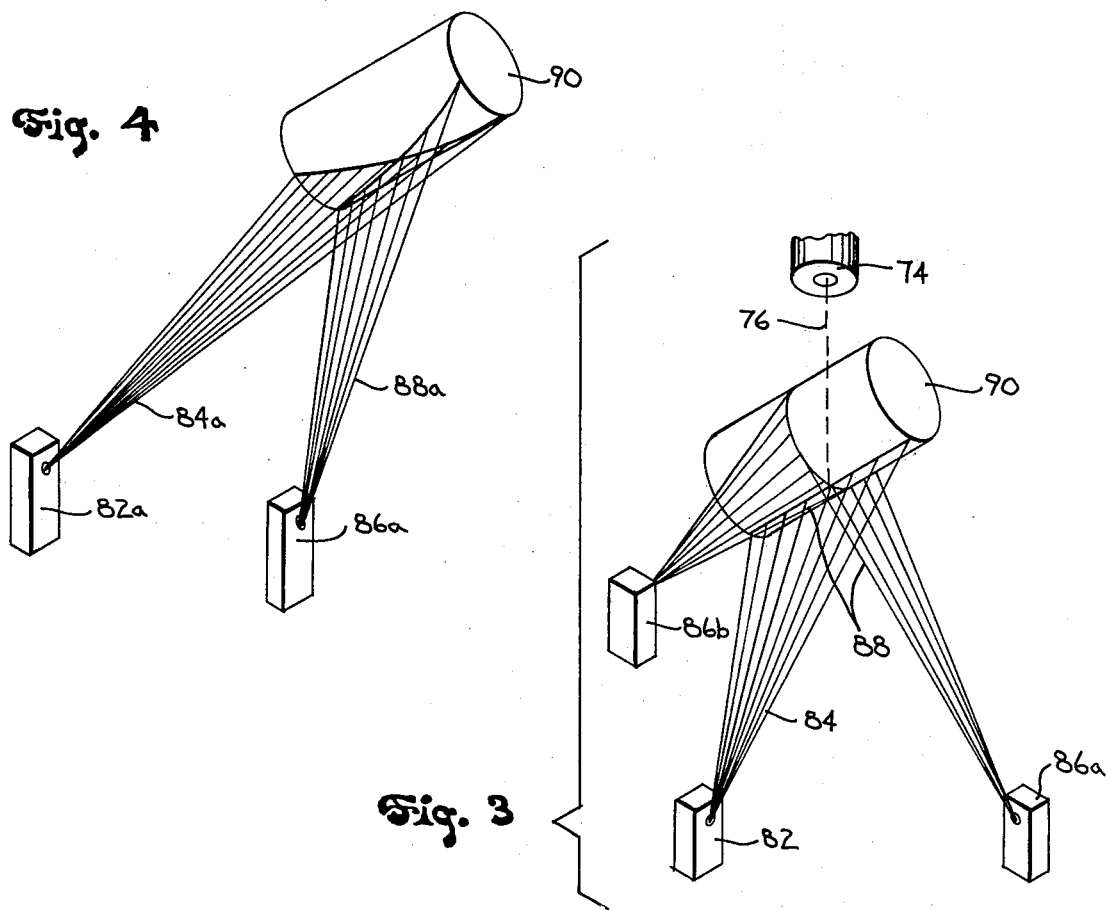

INDICATOR FOR USE WITH PROJECTED BEAM OF RADIATION

BACKGROUND OF THE INVENTION

1. Field of the Invention

The present invention is directed to an indicator for use with a projected beam employing a plurality of intersecting planes of light to obtain the indication.

2. Description of the Prior Art

Radiation therapy utilizes a beam of high energy radiation from a radiation source, such as a cobalt 60 supply or a linear accelerator. The portion of the patient to be treated is placed in the beam for a predetermined exposure time to obtain the desired therapeutic effect.

The radiation beam must be accurately positioned to ensure maximum benefit to the patient while minimizing undesirable side effects. Since the radiation beam is not visible to the human eye, various targeting devices have been utilized to ensure that the beam will impinge the correct portion of the patient. Typically, a target is placed on the patient's skin at the area to be treated. A light pattern, aligned with the path of the radiation beam, is positioned so that the light pattern is aligned with the target. The light pattern is then removed and the radiation beam established.

However, such a technique is often less than completely satisfactory. If the patient moves, for example, rolls about an axis normal to the radiation beam, diseased tissue within the body may move substantially out of the radiation beam but little misalignment can be noted. Even if the target and light pattern remain present during irradiation, the misalignment may not be detected. Under these circumstances, the effectiveness of the treatment may be substantially reduced.

Further, it is often necessary to ascertain the point at which the radiation beam exits the patient to insure that the patient and/or equipment are in proper alignment. Heretofore, a light has been mounted on the radiation source apparatus under the patient in opposition to the radiation beam to shine on the patient and mark the exit point of the radiation beam. However to properly position the light for all orientations of the radiation source is both expensive and awkward. In many cases, it restricts access to the patient by the medical personnel, preventing him/her from properly aligning the patient. The light is subject to damage from other equipment such as the patient bed.

The same concerns which apply to radiation therapy are also applicable to radiological diagnosis. That is, if the X-ray film sheet, patient and radiation beam are not properly positioned with respect to each other, the desired X-ray image on the film may not be obtained, requiring the X-ray to be taken over again and exposing the patient to additional radiation.

SUMMARY OF THE PRESENT INVENTION

It is, therefore, the object of the present invention to provide a means for indicating the relationship of a projected beam, such as a radiation beam, to an object, such as a patient or X-ray film holder, thereby to enhance radiological therapeutic or diagnostic techniques. Thus, the present invention may be used to position an X-ray film holder with respect to a radiation beam and a patient with respect to the film holder and beam for diagnostic X-rays. Or, the invention may be used to indicate the point at which a radiation beam enters, exits, or would exit a patient so that the positioning and orientation of the patent and the beam may be quickly and easily determined.

For these purposes, the present invention includes a light source for establishing a first plane of light containing the radiation beam in the plane and appliable to the object. A second light source establishes a second plane of light containing either the radiation beam or the object. The two planes of light intersect with the intersection defining the radiation beam-object relationship. For example, the second plane of light may be aligned with the path of travel of an X-ray film holder so that the intersection of the planes of light indicates a relationship between the holder and the radiation beam. Or, the second plane of light may contain the radiation beam so that the intersection is an indication of the relationship between the radiation beam and an object to which the planes are applied, such as a patient.

BRIEF DESCRIPTION OF THE DRAWING

FIG. 2 is a perspective view showing another embodiment of the invention used to indicate the relationship of a patient with respect to a radiation beam source.

FIG. 3 is a schematic perspective view showing details of the embodiment of FIG. 2 and its use in establishing the relationship between the projected beam and the patient.

FIG. 4 is a schematic perspective view of a modified embodiment of the invention of FIG. 2 showing its use in indicating the relationship between a radiation beam and a patient.

DETAILED DESCRIPTION OF THE PREFERRED EMBODIMENT

Figure 1:
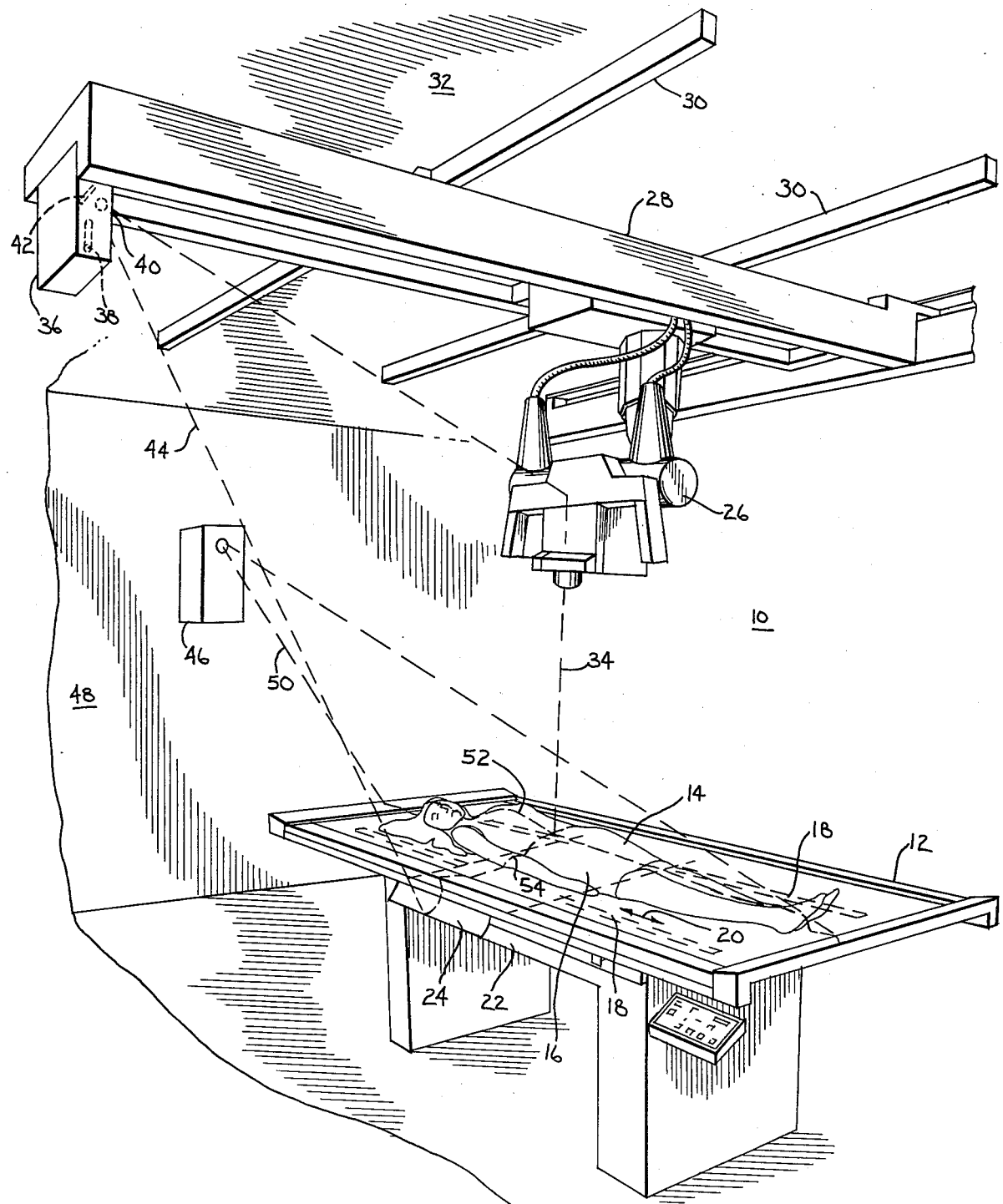
FIG. 1 is a perspective view showing one embodiment of the present invention used to orient an X-ray film holder, radiation beam source and patient.

FIG. 1 shows apparatus 10 for obtaining diagnostic X-rays. Apparatus 10 includes table 12 for receiving patient 14. A holder 16 for X-ray film is located beneath table 12. Holder 16 is movable back and forth, or in the head to toe direction with respect to patient 14, on means, such as rails 18, shown in FIG. 1. The direction of movement of film holder 16 is shown by the arrow 20. Holder 16 may be mounted in a carrier which extends from housing 22 under table 10 so as to form a handle 24 for moving film holder 16 and to permit insertion of film in the holder. If desired, table 12 may also move back and forth and from side to side to position the patient in a desired location without requiring him/her to shift position on the table. Film holder 16 does not move from side to side.

X-ray machine 26 is slidably mounted on beam 28 which, in turn, is slidably mounted on rails 30 fastened to the ceiling 32. X-ray machine 26 is rectilinearly movable by means of beam 28 and rails 30. X-ray machine 26 projects a beam of radiation vertically downward toward table 12. The axis of the beam of radiation is indicated schematically by 34 which also defines the path of a localizing light in X-ray machine 26.

The indicating means of the present invention includes a means for establishing a first plane of light containing the radiation beam and axis 34. Light source 36 preferably projects a visible plane of light and a laser source 38 having an anamorphic lens or line generator 40 which forms the beam of light from laser 38 reflected off mirror 42 into diverging rays lying in a single plane may be used. It will be appreciated that other types of radiant energy, such as infrared; other types of sources, such as incandescent; or other types of line generators, such as an aperture may be used. The foregoing terms, are thus intended to include all suitable types and sources of radiant energy and line generators as may be used in the light source.

The plane of light generated by light source 36 is indicated by the numeral 44 in FIG. 1. The light plane is vertical in orientation and is so projected so as to contain axis 34 of the radiation beam of X-ray machine 26. For this purpose, light source 36 may be mounted on the end of beam 28. Light plane 44 is also applied to table 12 and particularly to the handle 24 of the X-ray film carrier extending from housing 22, as shown in FIG. 1.

A second light source 46 is mounted on wall 48. Light source 46 may be similar in construction to light source 32 to project a second vertically oriented plane of light 50. Light source 46 is so positioned on wall 48 that second plane of light 50, when applied to table 12, lies along the center of film holder 16 in its path of movement on rails 18.

As shown in FIG. 1, light planes 44 and 50 will intersect on table 12, the angle of intersection in the embodiment of the invention shown in FIG. 1 being 90°.

In use, light sources 36 and 46 are energized to provide first and second light planes 44 and 50. Second light plane 50 falls on table 12 and patient 14 and forms a luminous line 52 on the table or patient which demarcates the center line of film holder 16 in its path of movement on rails 18. Line 52 serves to reference patient 14 to the center of film holder 16. Table 12, or patient 14, are moved so that the patient occupies the desired relative position with respect to the film holder. First light plane 44 also falls on table 12 and patient 14 to form line 54. The film holder carrier is then moved or beam 28 is moved on rails 30 until the line 54 formed by the impingement of plane 44 on film carrier handle 24 is in the desired relative location, for example, longitudinally centered on the handle. When so positioned, line 52 and line 54 will cross over the center of the film in holder 16. This intersection may be used to move X-ray machine 26 on beam 28 so that axis 34 of the radiation beam is centered over this intersection, as indicated by the localizing light. X-ray machine 26 is then operated to obtain the necessary X-ray on the film in holder 16.

FIG. 2 shows another embodiment of the present invention. A radiation beam source 70 includes arm 72 which supports head 74 for emitting radiation along a beam axis indicated schematically by 76. Arm 72 is arcuately movable on base 78 by ring 80 so as to rotate the axis 76 of the radiation beam and apply the radiation to a patient when positioned on table 12 with a desired degree of obliqueness for therapeutic purposes.

The radiation beam indicator of this embodiment includes a means for establishing a first plane of light containing radiation beam axis 76. A light source 82 may be used for this purpose. Light source 82 may be mounted on ring 80 of apparatus 70 so as to be movable with head 74 thereby to retain radiation beam axis 76 in plane 84 of light source 82 as arm 72 and head 74 are rotated. Light source 82 may be constructed in a manner similar to light sources 36 and 46.

Means are also provided to establish a second plane of light containing radiation beam axis 76. This means may typically be additional light sources 86a and 86b mounted on the floor or walls of the room containing radiation beam source 70. In the embodiment of the invention shown in FIGS. 2 and 3, light sources 86a and 86b, provide co-planar light planes which establish plane 88 lying at right angles to plane 84 and containing radiation beam 76.

FIG. 3 shows the operation of the indicator of the present invention in an application involving ascertaining the point at which radiation beam axis 76, applied from above, exits below a patient, schematically shown as a cylinder 90 in FIG. 3. Light source 82 is energized to provide light plane 84 which is applied to the underside of patient 90. Light source 86a and 86b are similarly energized to provide light plane 88. Light sources 86a and 86b are so mounted on the walls or floor of the room that plane 88 is also applied to the lower side of patient 90. Inasmuch as both planes 84 and 88 contain radiation beam axis 76, the intersection of these planes will mark the exit point of radiation beam 76 from patient 90 so that this point may be visually observed. Table 14 may have a removable panel 92 or a transparent portion to permit application of light planes 84 and 88 to the patient.

Should arm 72 and head 74 be rotated on base 78, plane 84 will be similarly rotated, maintaining the indication of the exit point. Light sources 86a and 86b are arranged so that light plane 88 is applied to a sufficient portion of the body to accommodate the rotation of arm 72 and head 74. An additional light source 86 may be mounted in the ceiling so that the plane of light 88 formed by this additional source and sources 86a and 86b extend entirely around the patient. A single light source 86 mounted in the floor of the room under table 14 may also be used instead of the pair of light sources 86a and 86b.

FIG. 4 shows another embodiment of the present invention in which the intersecting light planes 84a and 88a are oriented at an angle of less than 90°. Light source 82a provides light plane 84a. Only a single light source 86a is used for light plane 88a. Both light planes contain radiation beam axis 76 and are applied to the underside of patient 90. The intersection of light planes 84a and 88a indicates the exit point of beam 76 from patient 90.

In the manner shown in FIG. 2, light sources 82a and 86a may be mounted for rotation with head 72 so as to maintain the indication of the exit point as arm 72 is rotated with respect to the patient.

Various modes of carrying out the invention are contemplated as being within the scope of the following claims particularly pointing out and distinctly claiming the subject matter which is regarded as the invention.

I claim:

1. Apparatus for defining the relationship of a projected beam with respect to an object comprising:
a first light source means (36, 82) for establishing a first plane of light (44, 84) containing the projected beam (34, 76) and applicable to the object (14, 16, 24, 90); and
a second light source means (46, 86) for establishing a second plane of light (50, 88) containing at least one of the projected beam and object and appliable to the latter,
said first light source means (36, 82) being movable with respect to said second light plane (50, 88) and object (14, 16, 24, 90) while maintaining the projected beam (34, 76) therein, said first and second light planes intersecting, the intersection of said light planes defining the projected beam-object relationship.

2. Apparatus according to claim 1 further defined as apparatus for defining the relationship of a projected beam comprising X-rays or gamma rays with respect to the object.

3. Apparatus according to claim 1 wherein said first and second light source means are so oriented that said first and second light planes intersect at a predetermined angle.

4. Apparatus according to claim 3 wherein said first and second light source means are so oriented that said first and second light planes intersect at an angle of 90°.

5. Apparatus according to claim 2 wherein said second plane contains said object in a predetermined plane-object orientation.

6. Apparatus according to claim 5 further defined as defining the beam-object relationship when said object is movable with respect to said second light plane.

7. Apparatus according to claim 6 wherein apparatus defines said relationship when said object is movable along said second plane.

8. Apparatus according to claim 1, 4, or 6, further defined as means for defining the relationship of a radiation beam (34) with respect to a film holder (16).

9. Apparatus according to claim 1 wherein said second light plane (88) contains said projected beam for indicating, by the intersection of said light planes, a point of surface transit between the projected beam (34) and the surface of an object (70) inserted therein.

10. Apparatus according to claim 9 wherein at least one of said light planes is formed by a plurality of light source means (86a, b) angularly spaced about said object for establishing a plane of light appliable to the object along a desired portion of its surface.

11. Apparatus according to claim 10 wherein said one light plane is formed by at least a pair of light sources (86a, b).

12. Apparatus according to claim 9 further defined as a means indicating the exit of a radiation beam (76) with respect to a patient inserted therein, wherein said light planes are appliable to the patient and wherein the intersection of said first and second light planes indicates the exit of said beam.

13. Apparatus according to claim 12 wherein the radiation beam is movable with respect to the patient and said first light source means (82) is movable to maintain said beam in the said first light plane (84) and the indication of the point of exit.

* * * * *